US011969542B2

(12) United States Patent  
Locke et al.

(10) Patent No.: US 11,969,542 B2  
(45) Date of Patent: Apr. 30, 2024

(54) SYSTEM AND APPARATUS FOR PREVENTING THERAPY UNIT CONTAMINATION

(71) Applicant: KCI Licensing, Inc., San Antonio, TX (US)

(72) Inventors: Christopher Brian Locke, San Antonio, TX (US); Benjamin A. Pratt, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 18/213,227

(22) Filed: Jun. 22, 2023

(65) Prior Publication Data

US 2023/0330316 A1   Oct. 19, 2023

Related U.S. Application Data

(63) Continuation of application No. 17/292,662, filed as application No. PCT/US2019/057137 on Oct. 21, 2019, now abandoned.

(60) Provisional application No. 62/769,487, filed on Nov. 19, 2018.

(51) Int. Cl.  
*A61M 1/00*   (2006.01)  
*A61F 13/05*   (2024.01)

(52) U.S. Cl.  
CPC ............... *A61M 1/78* (2021.05); *A61F 13/05* (2024.01); *A61M 1/784* (2021.05); *A61M 1/98* (2021.05); *A61M 1/92* (2021.05)

(58) Field of Classification Search  
CPC .......... A61M 1/78; A61M 1/784; A61F 13/05  
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Philip R Wiest  
*Assistant Examiner* — Matthew Wrubleski (57) ABSTRACT

In some examples, provided is a fluid blockage device for use with a reduced-pressure source for treating a tissue site with reduced pressure. The fluid blockage device may be configured to preclude fluid communication through a port fluidly coupled to the reduced-pressure source when the fluid blockage device contacts a liquid. Other devices, systems, and methods are disclosed.

17 Claims, 6 Drawing Sheets

(56) References Cited

U.S. PATENT DOCUMENTS

| | | |
|---|---|---|
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,780,309 B2 * | 8/2004 | Haldopoulos .......... B01D 35/30 604/405 |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2010/0000933 A1 * | 1/2010 | Zuk, Jr. ................ B01D 63/087 210/406 |
| 2014/0163491 A1 | 6/2014 | Schuessler et al. |
| 2015/0080788 A1 | 3/2015 | Blott et al. |
| 2019/0030219 A1 * | 1/2019 | Kantola .................. A61M 1/66 |
| 2020/0345903 A1 * | 11/2020 | Selby .................... A61M 1/984 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| NO | 90/010424 A1 | 9/1990 |
| SG | 71559 | 4/2002 |
| WO | 80/02182 A1 | 10/1980 |
| WO | 87/04626 A1 | 8/1987 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

(56) References Cited

FOREIGN PATENT DOCUMENTS

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

* cited by examiner

SYSTEM AND APPARATUS FOR PREVENTING THERAPY UNIT CONTAMINATION

RELATED APPLICATIONS

The present application is a continuation of U.S. patent application Ser. No. 17/292,662, entitled "System and Apparatus for Preventing Therapy Unit Contamination," filed May 10, 2021, which is a U.S. National Stage Entry of PCT/US2019/057137, filed Oct. 21, 2019, entitled "System and Apparatus for Preventing Therapy Unit Contamination," which claims the benefit, under 35 USC § 119(e), of U.S. Provisional Patent Application U.S. Provisional Patent Application No. 62/769,487, entitled "System and Apparatus for Preventing Therapy Unit Contamination," filed Nov. 19, 2018, which is incorporated herein by reference for all purposes.

TECHNICAL FIELD

The invention set forth in the appended claims relates generally to tissue treatment systems, and more particularly, but without limitation, to systems, apparatus, and methods configured to prevent contamination of a therapy unit suitable for treating a tissue site.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating a tissue site in a negative-pressure therapy environment are set forth in the appended claims. Illustrative embodiments are also provided to enable a person skilled in the art to make and use the claimed subject matter.

In some example embodiments, a system for treating a tissue site may include a dressing, a reduced-pressure source, and a canister assembly. The dressing may be configured to be positioned in contact with the tissue site. The reduced-pressure source may be configured to be in fluid communication with the dressing. The canister assembly may be configured to be in fluid communication between the dressing and the reduced-pressure source. The canister assembly may include a fluid canister, a canister lid, a fluid entry port, a reduced-pressure port, and a fluid blockage device. The fluid canister may have an internal volume configured to receive fluid from the tissue site. The canister lid may be configured to provide a sealed enclosure relative to the fluid canister when the canister lid is sealingly engaged with the fluid canister. The fluid entry port may be configured to provide fluid communication between the sealed enclosure and the dressing. The reduced-pressure port may include an inlet and an outlet configured to provide fluid communication between the sealed enclosure and the reduced-pressure source. The inlet may be configured to face the sealed enclosure and the outlet may be configured to face the reduced-pressure source. The fluid blockage device may be configured to preclude fluid communication through the reduced-pressure port when exposed to a liquid.

In some example embodiments, a canister assembly for treating a tissue site with reduced-pressure may include a fluid canister, a canister lid, a reduced-pressure port, and a fluid blockage device. The fluid canister may have an internal volume configured to receive fluid from the tissue site. The canister lid may be configured to provide a sealed enclosure relative to the fluid canister when the canister lid is sealingly engaged with the fluid canister. The reduced-pressure port may include an inlet and an outlet configured to provide fluid communication with the sealed enclosure. The inlet may be configured to face the sealed enclosure and the outlet may be configured to face outward from the sealed enclosure. The fluid blockage device may be configured to preclude fluid communication through the reduced-pressure port when exposed to a liquid.

In some example embodiments, a fluid blockage device for treating a tissue site with reduced pressure may include a carrier, a primary filter, and an absorbent. The carrier may include a fitting configured to be coupled in fluid communication with a reduced-pressure source, and a flared opening in fluid communication with the fitting. The primary filter may be positioned at the flared opening of the carrier and configured to be in fluid communication between the tissue site and the fitting. The absorbent material may be in fluid communication between the fitting and the primary filter. The absorbent material may be configured to swell when exposed to a liquid.

In some example embodiments, a fluid blockage device for use with a reduced-pressure source for treating a tissue site with reduced pressure may include an absorbent material configured to be positioned in fluid communication between the reduced-pressure source and the tissue site. The absorbent material may be configured to swell and to preclude fluid communication between the reduced-pressure source and the tissue site when the absorbent material is exposed to a liquid.

In some example embodiments, a fluid blockage device for use with a reduced-pressure source for treating a tissue site with reduced pressure may be configured to preclude fluid communication through a port fluidly coupled to the reduced-pressure source when the fluid blockage device contacts a liquid.

Objectives, advantages, and a preferred mode of making and using the claimed subject matter may be understood best by reference to the accompanying drawings in conjunction with the following detailed description of illustrative example embodiments.

DESCRIPTION OF EXAMPLE EMBODIMENTS

The following description discloses non-limiting, illustrative example embodiments with sufficient detail to enable a person skilled in the art to make and use the subject matter set forth in the appended claims. Details that are well-known or not necessary for the skilled person to make and use the claimed subject matter may be omitted.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
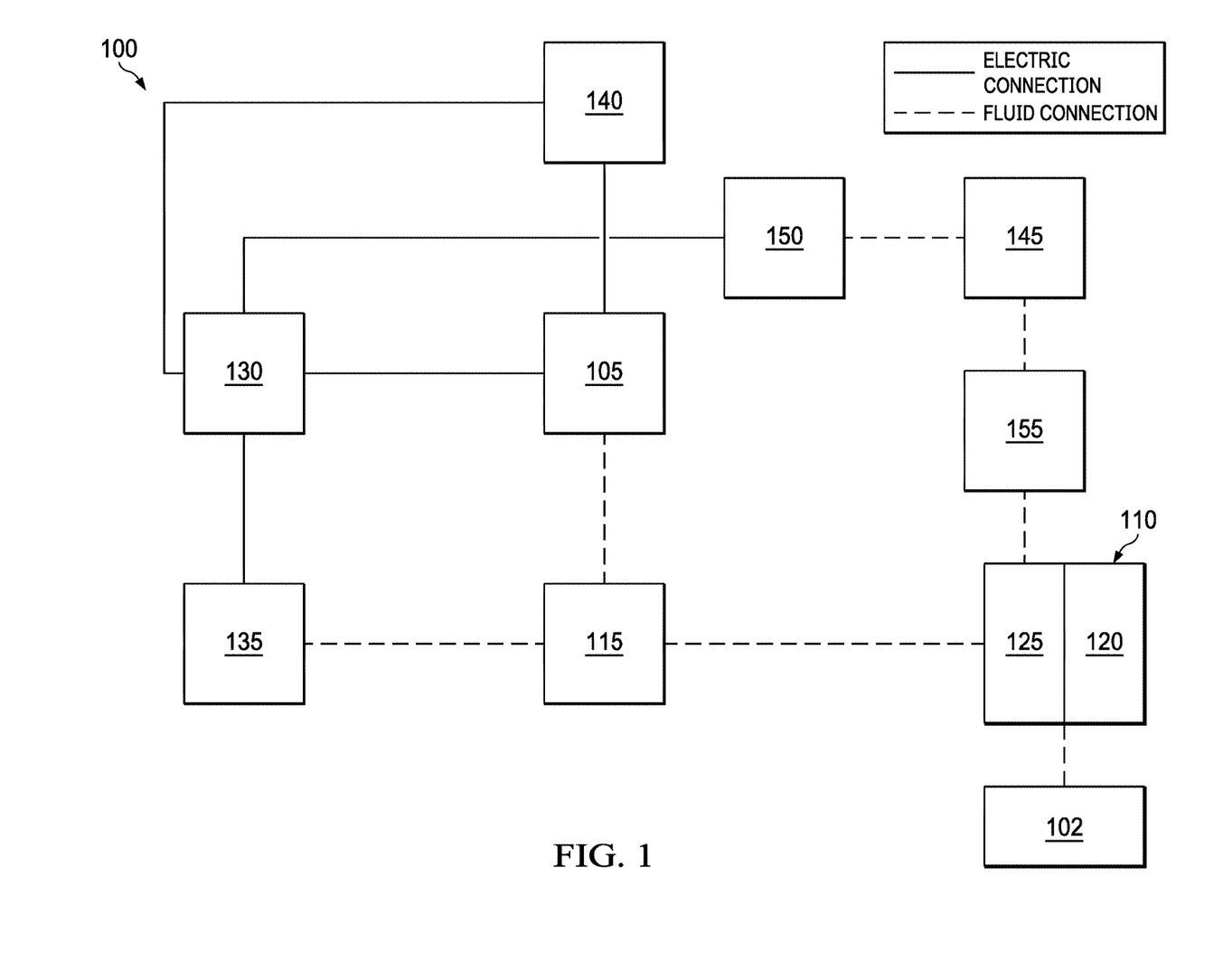
FIG. 1 is a block diagram of an example embodiment of a therapy system suitable for providing negative-pressure treatment and instillation treatment in accordance with this disclosure.

FIG. 1 is a block diagram of an example embodiment of a therapy system 100 that can provide negative-pressure therapy with instillation of topical treatment solutions to a tissue site, such as a tissue site 102, in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C.™ Pad available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

The therapy system 100 may also include a source of instillation solution. For example, a solution source 145 may be fluidly coupled to the dressing 110, as illustrated in the example embodiment of FIG. 1. The solution source 145 may be fluidly coupled to a positive-pressure source such as a positive-pressure source 150, a negative-pressure source such as the negative-pressure source 105, or both in some embodiments. A regulator, such as an instillation regulator 155, may also be fluidly coupled to the solution source 145 and the dressing 110 to ensure proper dosage of instillation solution (e.g. saline) to a tissue site. For example, the instillation regulator 155 may comprise a piston that can be pneumatically actuated by the negative-pressure source 105 to draw instillation solution from the solution source during a negative-pressure interval and to instill the solution to a dressing during a venting interval. Additionally or alternatively, the controller 130 may be coupled to the negative-pressure source 105, the positive-pressure source 150, or both, to control dosage of instillation solution to a tissue site. In some embodiments, the instillation regulator 155 may also be fluidly coupled to the negative-pressure source 105 through the dressing 110, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130, the solution source 145, and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may comprise or consist essentially of a manifold. A manifold in this context may comprise or consist essentially of a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 120 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 120 may also vary according to needs of a prescribed therapy. For example, the tensile strength of foam may be increased for instillation of topical treatment solutions. The 25% compression load deflection of the tissue interface 120 may be at least 0.35 pounds per square inch, and the 65% compression load deflection may be at least 0.43 pounds per square inch. In some embodiments, the tensile strength of the tissue interface 120 may be at least 10 pounds per square inch. The tissue interface 120 may have a tear strength of at least 2.5 pounds per inch. In some embodiments, the tissue interface may be foam comprised of polyols such as polyester or polyether, isocyanate such as toluene diisocyanate, and polymerization modifiers such as amines and tin compounds. In some examples, the tissue interface 120 may be reticulated polyurethane foam such as found in GRANUFOAM™ dressing or V.A.C. VERAFLO™ dressing, both available from Kinetic Concepts, Inc. of San Antonio, Texas.

The thickness of the tissue interface 120 may also vary according to needs of a prescribed therapy. For example, the thickness of the tissue interface may be decreased to reduce tension on peripheral tissue. The thickness of the tissue interface 120 can also affect the conformability of the tissue interface 120. In some embodiments, a thickness in a range of about 5 millimeters to 10 millimeters may be suitable.

The tissue interface 120 may be either hydrophobic or hydrophilic. In an example in which the tissue interface 120 may be hydrophilic, the tissue interface 120 may also wick fluid away from a tissue site, while continuing to distribute negative pressure to the tissue site. The wicking properties of the tissue interface 120 may draw fluid away from a tissue site by capillary flow or other wicking mechanisms. An example of a hydrophilic material that may be suitable is a polyvinyl alcohol, open-cell foam such as V.A.C. WHITEFOAM™ dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

In some embodiments, the tissue interface 120 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 120 may further serve as a scaffold for new cell-growth, or a scaffold material may be used in conjunction with the tissue interface 120 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S. A., Colombes, France; and Inspire 2301 and Inspire 2327 polyurethane films, commercially available from Expopack Advanced Coatings, Wrexham, United Kingdom. In some embodiments, the cover 125 may comprise INSPIRE 2301 having an MVTR (upright cup technique) of 2600 g/m$^2$/24 hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 145 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

The process of reducing pressure may be described illustratively herein as "delivering," "distributing," or "generating" negative pressure, for example. In general, exudate and other fluid flow toward lower pressure along a fluid path. Thus, the term "downstream" may refer to a location in a fluid path relatively closer to a source of negative pressure or further away from a source of positive pressure. Conversely, the term "upstream" may refer to a location further away from a source of negative pressure or closer to a source of positive pressure.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

Further, in some embodiments, the controller 130 may receive and process data, such as data related to instillation solution provided to the tissue interface 120. Such data may include the type of instillation solution prescribed by a clinician, the volume of fluid or solution to be instilled to a tissue site ("fill volume"), and the amount of time prescribed for leaving solution at a tissue site ("dwell time") before applying a negative pressure to the tissue site. The fill volume may be, for example, between 10 and 500 mL, and the dwell time may be between one second to 30 minutes. The controller 130 may also control the operation of one or more components of the therapy system 100 to instill solution. For example, the controller 130 may manage fluid distributed from the solution source 145 to the tissue interface 120. In some embodiments, fluid may be instilled to a tissue site by applying a negative pressure from the negative-pressure source 105 to reduce the pressure at the tissue site, drawing solution into the tissue interface 120. In some embodiments, solution may be instilled to a tissue site by applying a positive pressure from the positive-pressure source 150 to move solution from the solution source 145 to the tissue interface 120. Additionally or alternatively, the solution source 145 may be elevated to a height sufficient to allow gravity to move solution into the tissue interface 120.

Figure 2:
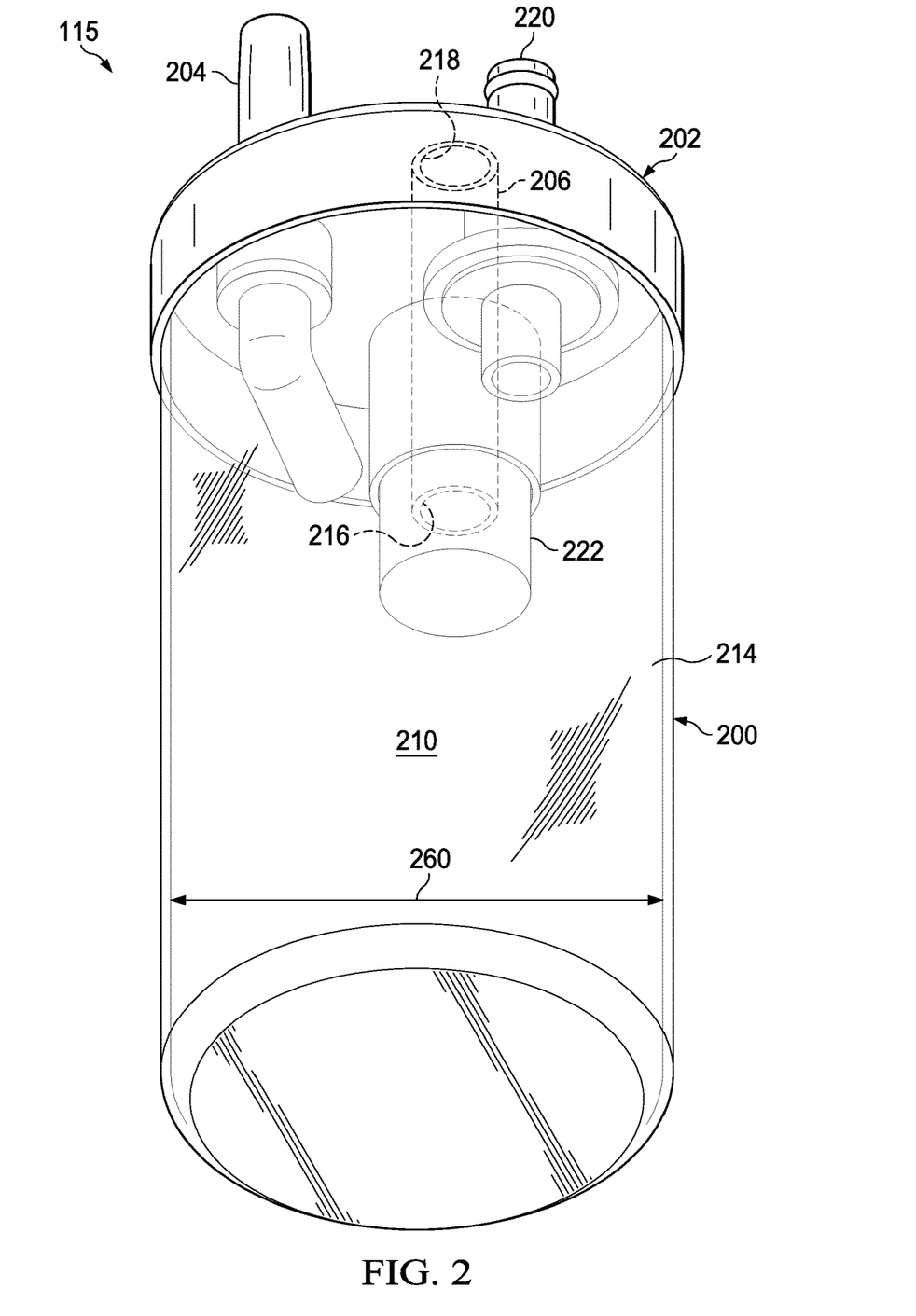
FIG. 2 is a perspective, exploded view of an example embodiment of a canister assembly that may be associated with some embodiments of the therapy system of FIG. 1.
Figure 3:
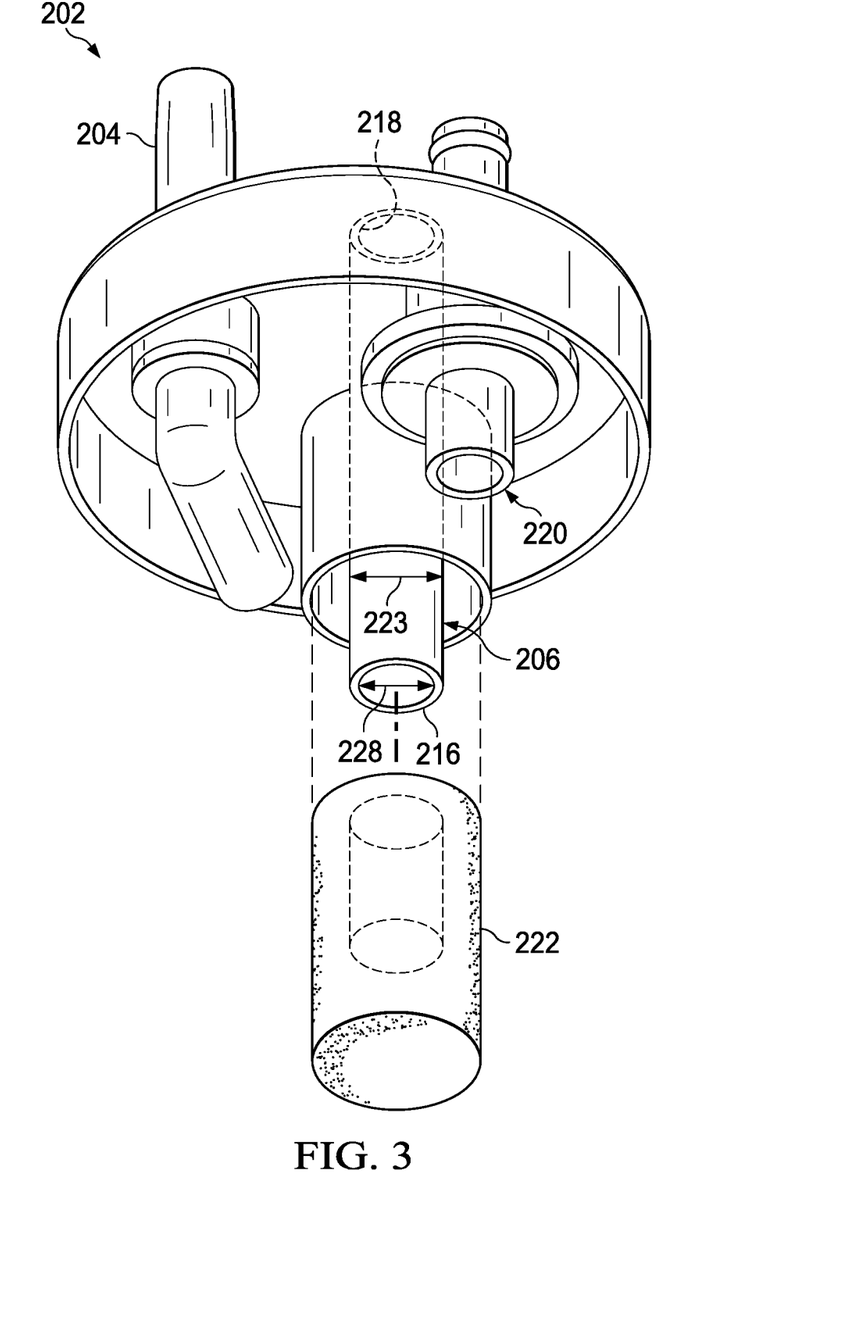
FIG. 3 is a perspective, exploded view of an example embodiment of a canister lid that may be associated with some embodiments of the canister assembly of FIG. 2.

Referring to FIGS. 1-2, in some example embodiments, the therapy system 100 may include the dressing 110, the negative-pressure source 105, and the container 115. The dressing 110 may be configured to be positioned in contact with the tissue site 102. The negative-pressure source 105 may be referred to as a reduced-pressure source 105 and may be configured to be in fluid communication with the dressing 110. The container 115 may be an assembly, in part or in whole, and may be referred to as a canister assembly 115. The dressing 110 may be configured to distribute a reduced pressure to the tissue site 102 that is communicated from the reduced-pressure source 105 through the canister assembly 115.

Referring to FIGS. 1-4, in some embodiments, the canister assembly 115 may include a fluid canister 200, a canister lid 202, a fluid entry port 204, a reduced-pressure port 206, and a fluid blockage device 208. One or more elements of the canister assembly 115 may be removed or additional elements may be added as described herein depending on therapeutic requirements or preferences.

The canister assembly 115 may be configured to be positioned in fluid communication between the dressing 110 and the reduced-pressure source 105. For example, the reduced-pressure source 105 may be configured to be coupled in fluid communication with the reduced-pressure port 206, and the dressing 110 may be configured to be coupled in fluid communication with the fluid entry port 204 of the canister assembly 115. The fluid entry port 204 may be in fluid communication with the reduced-pressure port 206 through the sealed enclosure 214 of the canister assembly 115 such that the reduced-pressure source 105 is coupled in fluid communication with the dressing 110 and the tissue site 102 through the sealed enclosure 214.

The fluid canister 200 may have an internal volume 210 configured to receive fluid, such as fluid from the tissue site 102. The canister lid 202 may be configured to provide a sealed enclosure 214 relative to or in combination with the fluid canister 200 when the canister lid 202 is sealingly engaged with the fluid canister 200. In some embodiments, the canister lid 202 may be permanently sealed to the fluid canister 200. The fluid entry port 204 may be configured to provide fluid communication between the sealed enclosure 214 and the dressing 110.

The reduced-pressure port 206 may include an inlet 216 and an outlet 218 configured to provide fluid communication between the sealed enclosure 214 and the reduced-pressure source 105. The inlet 216 may be configured to face the sealed enclosure 214 and the outlet 218 may be configured to face the reduced-pressure source 105 or to face outward from the sealed enclosure 214. The fluid blockage device 208 may be positioned at or between the inlet 216 and the outlet 216 of the reduced-pressure port 206. Further, the fluid blockage device 208 may be configured to preclude fluid communication through the reduced-pressure port 206 when exposed to a liquid as described further herein.

In some examples, the therapy system 100 may include a pressure feedback port 220 configured to be in fluid communication with the sealed enclosure 214 and to provide a pressure signal corresponding to a pressure in the sealed enclosure 214. The pressure feedback port 220 may be configured to provide a pressure feedback signal to the controller 130 directly or through a pressure sensor, such as the first sensor 135. In some examples, the canister lid 202 may carry the fluid entry port 204, the pressure feedback port 220, and the reduced-pressure port 206. In some examples, the fluid entry port 204, the pressure feedback port 220, and the reduced-pressure port 206 may be fluidly disposed through the canister lid 202.

Further, in some examples, the therapy system 100 may include a primary filter 222 configured to be in fluid communication between the sealed enclosure 214 and the reduced-pressure source 105. The primary filter 222 may be hydrophobic and may include a sintered, hydrophobic polymer having various sizes, shapes, and configurations as shown in FIGS. 2-6, for example. The primary filter 222 may be directly exposed to the internal volume 210 of the fluid canister 200 and any liquid present in the sealed enclosure 214 during operation. The reduced-pressure port 206 may carry the primary filter 222 proximate to or at the inlet 216 of the reduced-pressure port 206. In some examples, the primary filter 222 may be sized to fit around an external diameter 223 of the reduced-pressure port 206 as shown in FIGS. 2-5.

Figure 4:
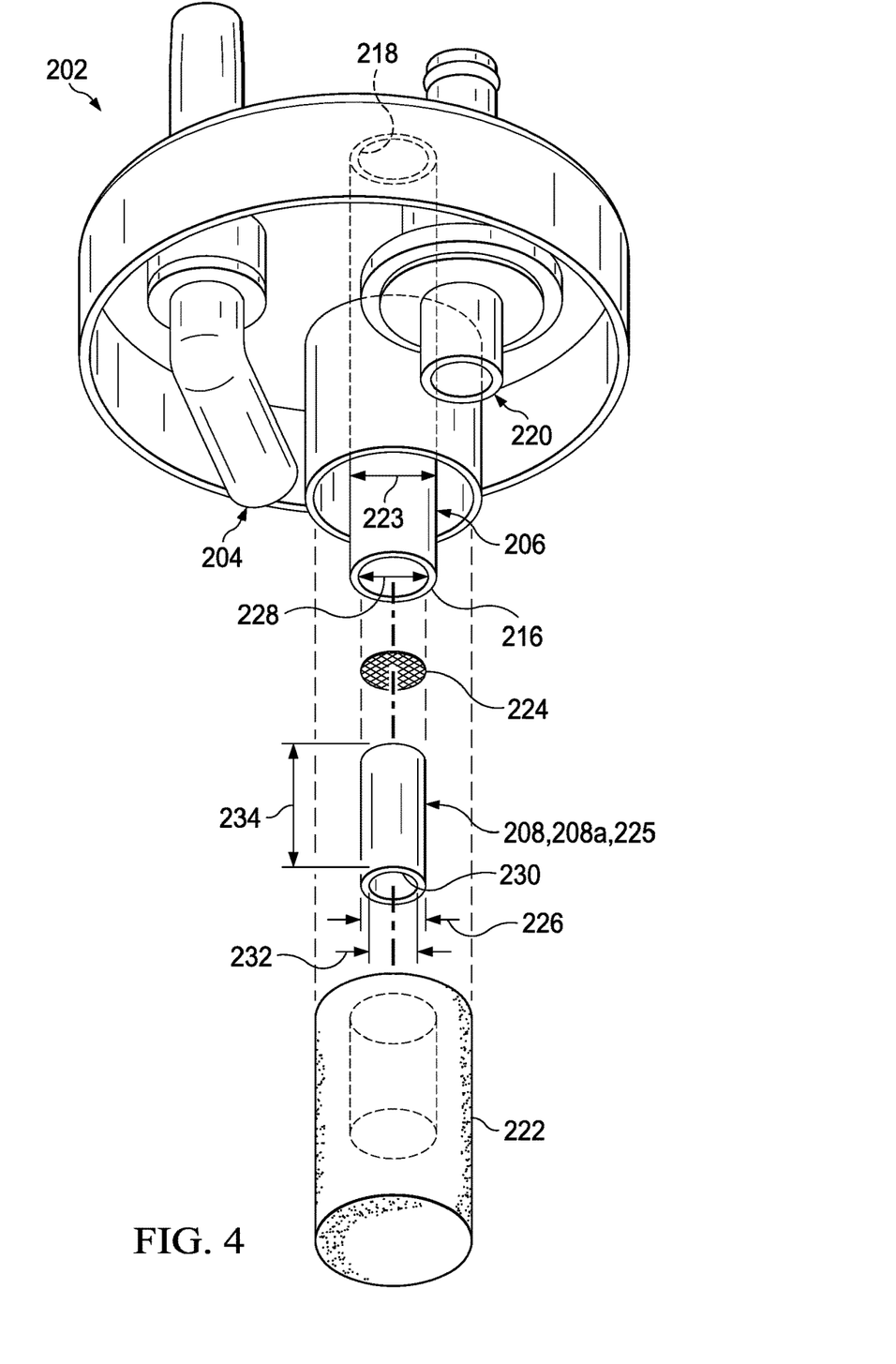
FIG. 4 is a perspective, exploded view of an example embodiment of a fluid blockage device suitable for use with some embodiments of the canister assembly or therapy system according to this disclosure.
Figure 5:
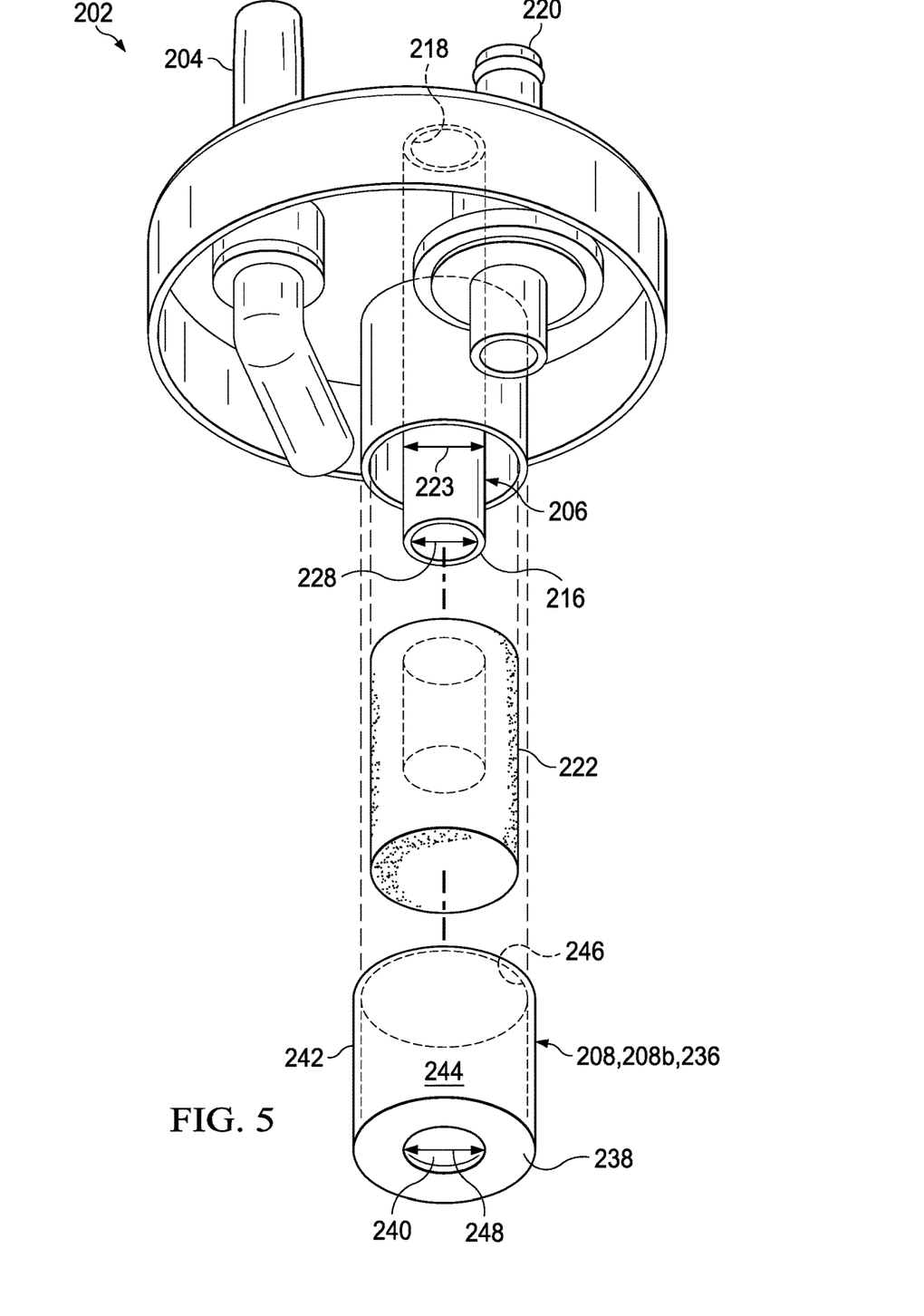
FIG. 5 is a perspective, exploded view of another example embodiment of a fluid blockage device suitable for use with some embodiments of the canister assembly or therapy system according to this disclosure.
Figure 6:
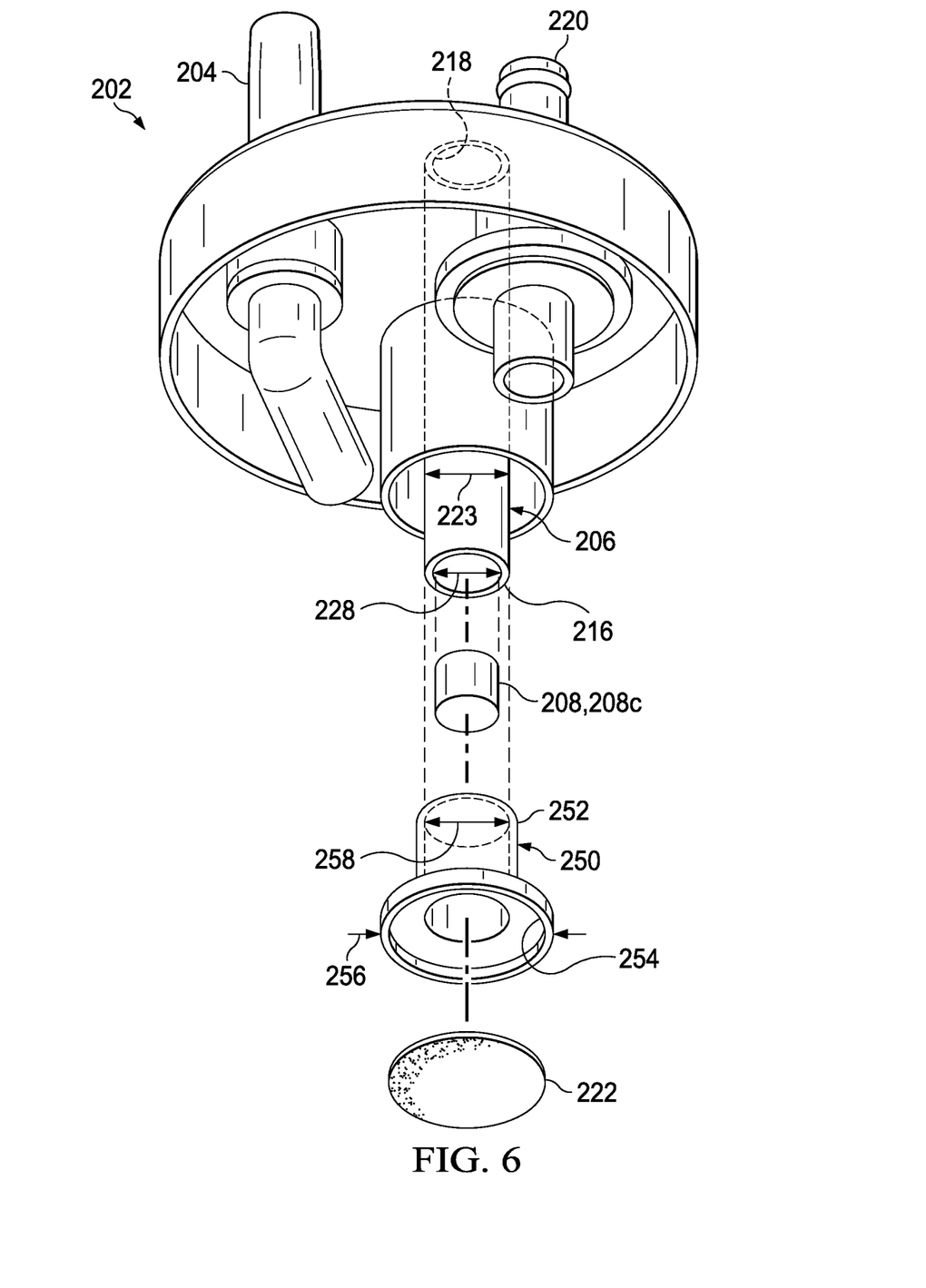
FIG. 6 is a perspective, exploded view of another example embodiment of a fluid blockage device suitable for use with some embodiments of the canister assembly or therapy system according to this disclosure.

FIGS. 4-6 depict various non-limiting example embodiments of the fluid blockage device 208. The fluid blockage device 208 may be configured to be positioned between the reduced-pressure source 105 and the tissue site 102. For example, the fluid blockage device 208 may be configured to be positioned in fluid communication between the outlet 218 of the reduced-pressure port 206 and the sealed enclosure 214, shown in FIG. 2. The fluid blockage device 208 may be operable to block or preclude fluid communication between the reduced-pressure source 105 and the tissue site 102 when certain operating conditions are encountered. For example, the fluid blockage device 208 may block fluid communication through the reduced-pressure port 206 to the reduced-pressure source 105, for example, when a level of liquid in the fluid canister 200 reaches the inlet 216 of the reduced-pressure port 206, when liquid splashes or overly saturates the primary filter 222, or the primary filter 222 experiences a failure. Such a configuration may trigger a system shut down alarm to protect components of the therapy system 100 from contamination or liquid exposure, such as the reduced-pressure source 105, electronic components, or other components that may be sensitive to liquid or bacterial exposure. The fluid blockage device 208 may also include, operate as, or be referred to as a secondary filter 208.

Referring to FIG. 4, in some examples, the fluid blockage device 208 may be a fluid blockage device 208a. The fluid blockage device 208a may be configured to be positioned in fluid communication between the primary filter 222 and the reduced-pressure source 105. In some examples, the fluid blockage device 208a may be positioned in fluid communication between the primary filter 222 and the outlet 218 of the reduced-pressure port 206. The fluid blockage device 208a may include or be formed of an absorbent material configured to swell when exposed to liquid. For example, the fluid blockage device 208a may include or be formed of a sintered, super absorbent polymer. Further, in some examples, the fluid blockage device 208a may include or be formed of a super absorbent polymer and charcoal.

In some examples, the fluid blockage device 208a may include or be formed as a tube 225 having an external diameter 226 sized to fit within and to engage an internal diameter 228 of the reduced-pressure port 206 between the inlet 216 and the outlet 218. The tube 225 may include an internal lumen 230 extending through opposing ends of the tube 225. The tube 225 may be configured to swell when in direct contact with a liquid such that the internal lumen 230 is blocked or occluded and the external diameter 226 of the tube 225 sealingly engages the internal diameter 228 of the reduced-pressure port 206, creating a blockage in the reduced-pressure port 206. In some examples, the internal lumen 230 of the tube 225 may have an internal diameter 232 between about 3.5 millimeters to about 7.2 millimeters. Further, in some examples, the tube 225 may have a length 234 between about 22 millimeters to about 26 millimeters. In some examples, the tube 225 of the fluid blockage device 208a may include or be formed of a molded slug of absorbent carboxymethyl cellulose granules, such as LUQUASORB®, available from BASF of Florham Park, New Jersey, USA.

In some examples, a filter membrane 224 may be positioned between the outlet 218 of the reduced-pressure port 206 and the fluid blockage device 208a and configured to retain the fluid blockage device 208a within the canister assembly 115 or the canister lid 202. In some examples, the filter membrane 224 may include or be formed of one or more of the following materials: a non-woven material and a cellulose material. In some examples, the filter membrane 224 may include or be formed of LIBELTEX TDL2 or LIBELTEX TL4 and may have a material density between about 80 gsm to about 150 gsm.

Referring to FIG. 5, in some examples, the fluid blockage device 208 may be a fluid blockage device 208b. The fluid blockage device 208b may include a protective housing 236. The protective housing 236 may include a base 238, a fluid aperture 240 disposed through the base 238, a side-wall 242 extending outward from and around the base 238 to form a chamber 244, and a chamber opening 246 sized to receive the reduced-pressure port 206 and the primary filter 222 within the chamber 244. The fluid aperture 240 may be disposed through the base 238 of the protective housing 236. In some examples, the base 238 having the fluid aperture 240 may be a component of the protective housing 236 having a maximum distance of extension from the reduced-pressure port 206 into the sealed enclosure 214. In some examples (not shown), the fluid aperture 240 may be biased toward the side-wall 242 of the protective housing 236, which may position the fluid aperture 240 in a substantially central location underneath the canister lid 202.

The fluid aperture 240 may be configured to provide fluid communication between the reduced-pressure port 206 and the sealed enclosure 214 until a liquid level in the sealed enclosure 214 reaches the fluid aperture 240 and blocks or occludes the fluid aperture 240. The protective housing 236 may be configured to surround and to cover the reduced-pressure port 206. In some examples, the fluid aperture 240 is configured to provide all fluid communication between the reduced-pressure port 206 and the sealed enclosure 214 such that a blockage of the fluid aperture 240 causes an entire blockage of all fluid communication between the reduced-pressure source 105 and the tissue site 102. In some examples, the fluid aperture 240 may have a diameter 248 between about 3 millimeters to about 5 millimeters. Shown as an illustrative example in FIG. 5, the protective housing 236 may be coupled around the inlet 216 of the reduced-pressure port 206 with an interference or compression fit.

The protective housing 236 may comprise, be formed of, or molded from any stable polymer material, such as, without limitation, polyethylene (PE) or acrylonitrile butadiene styrene (ABS).

Referring to FIG. 6, in some examples, the therapy system 100 may include a carrier 250 and the fluid blockage device 208 may be a fluid blockage device 208c. The fluid blockage device 208c may be used with the carrier 250 as part of the therapy system 100, or the carrier 250 may form part of the fluid blockage device 208c. The fluid blockage device 208c may be configured to be positioned in fluid communication between the primary filter 222 and the reduced-pressure source 105. Further, in some examples, the fluid blockage device 208c may be positioned in fluid communication between the primary filter 222 and the outlet 218 of the reduced-pressure port 206. As shown in FIG. 6, the primary filter 222 may have, without limitation, a circular or disc-like shape. Although shown as having a different shape, the primary filter 222 shown in FIG. 6 may be comprised of similar or analogous materials as the previously described examples of the primary filter 222.

The carrier 250 may include a fitting, such as a reduced-pressure port fitting 252, and a flared opening 254. The fitting or the reduced-pressure port fitting 252 may be configured to be coupled in fluid communication with the reduced-pressure source 105 through the reduced-pressure port 206, for example. The flared opening 254 may be in fluid communication with the fitting or the reduced-pressure port fitting 252 through the carrier 250. The flared opening 254 may have a flared diameter 256 larger than a fitting diameter 258 of the reduced-pressure port fitting 252. The fitting diameter 258 of the reduced-pressure port fitting 252 may be sized to fit over or around the external diameter 223 of the reduced-pressure port 206 to provide fluid communication between the reduced-pressure port 206 and the carrier 250. In some examples, the flared diameter 256 of the flared opening 254 may be substantially the same as an internal diameter 260 of the fluid canister 200, shown in FIG. 2, which may provide additional filtration surface area for preventing clogs or obstructions.

The primary filter 222 may be positioned at the flared opening 254 of the carrier 250. The primary filter 222 may be configured to be positioned in fluid communication between the tissue site 102 and the fitting or the reduced-pressure port fitting 252. For example, the primary filter 222 may be configured to be positioned in fluid communication between the sealed enclosure 214 and the fitting or the reduced-pressure port fitting 252. The fluid blockage device 208c may be configured to be positioned in fluid communication between the fitting or the reduced-pressure port fitting 252 and the primary filter 222. The fluid blockage device 208c may include or be formed of an absorbent material configured to swell when exposed to a liquid and to block fluid communication to the reduced-pressure source 105 through the reduced-pressure port. For example, the fluid blockage device 208c may include or be formed of a sintered, super absorbent polymer. Further, the fluid blockage device 208c may include or be formed of a super absorbent polymer and charcoal. Although the fluid blockage device 208c is shown in FIG. 6 as a cylindrical device sized for the reduced-pressure port 206, in other examples, the fluid blockage device 208c may fit within the carrier 250 and may take the form of a granules.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the controller 130 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A system for treating a tissue site, comprising:
    a dressing configured to be positioned in contact with the tissue site;
    a reduced-pressure source configured to be in fluid communication with the dressing; and
    a canister assembly configured to be in fluid communication between the dressing and the reduced-pressure source, the canister assembly comprising:
        a fluid canister having an internal volume configured to receive fluid from the tissue site,
        a canister lid configured to provide a sealed enclosure relative to the fluid canister,
        a fluid entry port configured to provide fluid communication between the sealed enclosure and the dressing,
        a reduced-pressure port including an inlet and an outlet configured to provide fluid communication between the sealed enclosure and the reduced-pressure source,
        a fluid blockage device configured to preclude fluid communication through the reduced-pressure port when exposed to a liquid, and
        a primary filter configured to be in fluid communication between the sealed enclosure and the reduced-pressure source, wherein the reduced-pressure port comprises an internal diameter and an external diameter, and wherein the fluid blockage device is sized to fit within and to engage the internal diameter of the reduced-pressure port and the primary filter is sized to fit around the external diameter of the reduced-pressure port.

2. The system of claim 1, wherein the fluid blockage device comprises an absorbent material configured to swell when exposed to the liquid.

3. The system of claim 1, wherein the fluid blockage device comprises a secondary filter.

4. The system of claim 1, wherein the fluid blockage device is configured to be positioned in fluid communication between the primary filter and the reduced-pressure source.

5. The system of claim 1, wherein the fluid blockage device is positioned in fluid communication between the primary filter and the outlet of the reduced-pressure port.

6. The system of claim 1, wherein the primary filter comprises a sintered, hydrophobic polymer.

7. The system of claim 1, wherein the fluid blockage device comprises a tube having an external diameter sized to fit within and to engage the internal diameter of the reduced-pressure port between the inlet and the outlet, wherein the tube comprises an internal lumen extending through opposing ends of the tube, and wherein the tube is configured to swell when in direct contact with the liquid such that the internal lumen is occluded and the external diameter of the tube sealingly engages the reduced-pressure port.

8. The system of claim 1, wherein the fluid blockage device comprises a protective housing including a fluid aperture configured to provide fluid communication between the reduced-pressure port and the sealed enclosure until a liquid level in the sealed enclosure occludes the fluid aperture.

9. The system of claim 8, wherein the protective housing is configured to surround and to cover the reduced-pressure port.

10. The system of claim 8, wherein the protective housing is coupled around the inlet of the reduced-pressure port.

11. The system of claim 8, wherein the protective housing comprises a base, a side-wall extending outward from and around the base to form a chamber, and a chamber opening sized to receive the reduced-pressure port and the primary filter within the chamber.

12. The system of claim 11, wherein the fluid aperture is disposed through the base of the protective housing at a maximum distance of extension from the reduced-pressure port into the sealed enclosure.

13. A canister assembly for treating a tissue site with reduced-pressure, comprising:
a fluid canister having an internal volume configured to receive fluid from the tissue site;
a canister lid configured to provide a sealed enclosure relative to the fluid canister when the canister lid is sealingly engaged with the fluid canister;
a reduced-pressure port including an inlet and an outlet configured to provide fluid communication with the sealed enclosure, wherein the inlet is configured to face the sealed enclosure and the outlet is configured to face outward from the sealed enclosure; and
a fluid blockage device configured to preclude fluid communication through the reduced-pressure port when exposed to a liquid, wherein the fluid blockage device comprises a tube having an external diameter sized to fit within and to engage an internal diameter of the reduced-pressure port between the inlet and the outlet, wherein the tube comprises an internal lumen extending through opposing ends of the tube, and wherein the tube is configured to swell when in contact with the liquid.

14. The canister assembly of claim 13, wherein the fluid blockage device comprises an absorbent material configured to swell when exposed to the liquid.

15. The canister assembly of claim 13, wherein the reduced-pressure port carries a primary filter at the inlet of the reduced-pressure port, and wherein the fluid blockage device is positioned between the inlet and the outlet of the reduced-pressure port.

16. The canister assembly of claim 15, wherein the fluid blockage device is positioned in fluid communication between the primary filter and the outlet of the reduced-pressure port.

17. A canister assembly for treating a tissue site with reduced-pressure, comprising:
a fluid canister having an internal volume configured to receive fluid from the tissue site;
a reduced-pressure port configured to provide fluid communication with the internal volume;
a fluid blockage device comprising a material configured to swell when exposed to a liquid;
a carrier comprising:
a reduced-pressure port fitting configured to be coupled in fluid communication with the reduced-pressure port,
a flared opening in fluid communication with the reduced-pressure port fitting, the flared opening having a flared diameter larger than a fitting diameter of the reduced-pressure port fitting; and
a primary filter positioned at the flared opening of the carrier and configured to be in fluid communication between the internal volume and the reduced-pressure port fitting;
wherein the fluid blockage device is configured to be positioned in fluid communication between the reduced-pressure port fitting and the primary filter.

* * * * *